(12) United States Patent
Vogt

(10) Patent No.: US 10,022,235 B2
(45) Date of Patent: Jul. 17, 2018

(54) MODULAR ARTICULAR SPACER SYSTEM

(71) Applicant: Heraeus Medical GmbH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 0 days.

(21) Appl. No.: 14/497,383

(22) Filed: Sep. 26, 2014

(65) Prior Publication Data

US 2015/0094822 A1 Apr. 2, 2015

(30) Foreign Application Priority Data

Sep. 27, 2013 (DE) .................... 10 2013 219 656

(51) Int. Cl.
*A61F 2/32* (2006.01)
*A61F 2/36* (2006.01)
(Continued)

(52) U.S. Cl.
CPC .................. *A61F 2/32* (2013.01); *A61F 2/36* (2013.01); *A61F 2/40* (2013.01);
(Continued)

(58) Field of Classification Search
CPC .. A61F 2/32; A61F 2/36; A61F 2/3601; A61F 2/3609; A61F 2002/365; A61F 2002/3652
See application file for complete search history.

(56) References Cited

U.S. PATENT DOCUMENTS 5,133,771 A * 7/1992 Duncan ............... A61F 2/30942
264/DIG. 30
5,653,765 A 8/1997 McTighe et al.
(Continued)

FOREIGN PATENT DOCUMENTS

CN 101965165 A 2/2011
CN 102088931 A 6/2011
(Continued)

OTHER PUBLICATIONS

Nord-Lock website screenshot from Dec. 2012.*
(Continued)

*Primary Examiner* — Thomas J Sweet
*Assistant Examiner* — Daniel Bissing
(74) *Attorney, Agent, or Firm* — Norris McLaughlin & Marcus P.A.

(57) ABSTRACT

A modular articulated spacer system provides for screw-based assembly of an articular spacer intended to replace an artificial joint temporarily, whereby the articulated spacer system comprises at least two modules connectable by means of a screw connection, whereby a first module of the articular spacer system comprises a surface for formation of a sliding surface of the joint of the articular spacer and a second module of the articular spacer system comprises a stem for connection to a bone. The modules are connectable by means of the screw connection comprising at last one screw-locking device for each screw connection, whereby the screw-locking device is connected to one of the modules or is provided in the form of the same part as one of the modules. A method builds-up an articular spacer using said articulated spacer system, in which the articular spacer is screwed together using at least two modules, whereby the modules are screwed together appropriately such that the screw-locking devices prevent the modules from detaching or being unscrewed.

18 Claims, 6 Drawing Sheets

(51) Int. Cl.
  *A61F 2/40* (2006.01)
  *A61F 2/30* (2006.01)
(52) U.S. Cl.
  CPC ............ *A61F 2002/30405* (2013.01); *A61F 2002/30514* (2013.01); *A61F 2002/30616* (2013.01); *A61F 2002/30672* (2013.01); *A61F 2002/30677* (2013.01); *A61F 2002/30919* (2013.01); *A61F 2002/365* (2013.01); *A61F 2002/3674* (2013.01); *Y10T 29/49963* (2015.01)

(56) References Cited

U.S. PATENT DOCUMENTS

| | | | |
|---|---|---|---|
| 2001/0008981 | A1 | 7/2001 | Masini |
| 2010/0087925 | A1* | 4/2010 | Kostuik ................ A61F 2/447 623/17.16 |
| 2011/0035021 | A1* | 2/2011 | Bergin ................ A61F 2/30734 623/22.42 |
| 2011/0218631 | A1* | 9/2011 | Woodburn, Sr. ........ A61F 2/442 623/17.16 |
| 2013/0072896 | A1* | 3/2013 | Faccioli ................ A61F 2/32 604/500 |
| 2014/0309745 | A1* | 10/2014 | Burnikel ................ A61F 2/4059 623/19.12 |

FOREIGN PATENT DOCUMENTS

| | | |
|---|---|---|
| EP | 0393608 A2 | 10/1990 |
| EP | 1166724 A1 | 1/2002 |
| JP | H10502284 A | 3/1998 |
| WO | 98/51240 A1 | 11/1998 |
| WO | 2010/015877 A1 | 2/2010 |
| WO | 2013/041906 A1 | 3/2013 |

OTHER PUBLICATIONS

Canadian Office Action for corresponding CA Application No. 2,861,915 dated Oct. 8, 2015.

European Search Report for corresponding EP Application No. 14183311.1 dated Jan. 28, 2015.

Japanese Office Action for corresponding JP Application No. 2014-195089 dated Sep. 7, 2015.

Australian Examination Report for corresponding AU Application No. 2014221263 dated Apr. 5, 2016.

Chinese Office Action for corresponding CN Application No. 201410486146.1 dated Mar. 2, 2016.

* cited by examiner

MODULAR ARTICULAR SPACER SYSTEM

The invention relates to a modular articular spacer system for screw-based assembly of an articular spacer intended to replacement an artificial joint temporarily, whereby the articular spacer system comprises at least two modules that can be connected by means of a screw connection, whereby a first module of the articular spacer system comprises a surface for formation of a sliding surface of the joint of the articular spacer and a second module of the articular spacer system comprises a stem for connection to a bone.

The invention also relates to a method for building-up an articular spacer using said articular spacer system and to the use of an articular spacer produced from said articular spacer system.

Articular endoprostheses currently have a service life of several years, for example on average more than ten and up to fifteen years in the case of cemented hip endoprostheses. However, undesirable loosening of the articular endoprostheses can occur before the end of the usual service life. This can concern either septic or aseptic loosening. Aseptic loosening means that no microbial germs are detectable yet. There are many causes of aseptic loosening. Aseptic loosening is often related to abrasion at the sliding surfaces of articular endoprostheses.

The loosening process in septic loosening is induced by microbial germs. This can either be early or late infections depending on the time of manifestation. Septic loosening is a very serious disease for the patient and its treatment is very expensive. It is customary to perform a revision surgery in cases of aseptic and septic loosening alike. This can proceed as a one-stage or a two-stage revision surgery. Two-stage revision surgeries are very common in cases of septic loosening.

In a two-stage revision surgery, the infected articular endoprosthesis is removed in a first surgery (OP) followed by debridement (removal of the infected tissue) and subsequent insertion of a temporary place-holder, a so-called spacer. Said spacer occupies for a number of weeks the space previously occupied by the revised endoprosthesis until the manifest infection has subsided. Said place-holder function is very important in order to effectively prevent muscular atrophy during this period of time and in order to stabilise the existing resection scenario.

There are non-articulating and articulating spacers available. Articulating spacers, referred to as articular spacers hereinafter, replicate the function of the joint and allow the afflicted limbs to have a certain degree of mobility. This allows the patient to be mobilised early. Therefore, the insertion of articular spacers is very popular currently. Mainly hip spacers, knee spacers, and elbow spacers are used as articular spacers. The spacer is removed in a second surgery, another debridement is done before implanting a cemented or cement-free revision articular endoprosthesis.

The use of spacers is originally based on the work of Hovelius and Josefsson (Hovelius L, Josefsson G (1979), "An alternative method for exchange operation of infected arthroplasty", Acta Orthop. Scand. 50: 93-96). Other early work on spacers includes Younger (Younger A S, Duncan C P, Masri B A, McGraw R W (1997), "The outcome of two-stage arthroplasty using a custom-made interval spacer to treat the infected hip", J. Arthroplasty 12: 615-623), Jones (Jones W A, Wroblewski B M (1989), "Salvage of failed total knee arthroplasty: the 'beefburger' procedure", J. Bone Joint Surg. Br. 71: 856-857), and Cohen (Cohen J C, Hozack W J, Cuckler J M, Booth R E Jr (1988), "Two-stage reimplantation of septic total knee arthroplasty, Report of three cases using an antibiotic-PMMA spacer block", J. Arthroplasty 3: 369-377). McPherson described a concept according to which spacers can be manufactured from bone cement exclusively (McPherson E J, Lewonowski K, Dorr L D (1995), "Techniques in arthroplasty. Use of an articulated PMMA spacer in the infected total knee arthroplasty", J. Arthroplasty 10: 87-89).

Currently, a number of pre-made articulating hip and knee spacers based on polymethylmethacrylate bone cement doped with gentamicin and/or vancomycin is commercially available. Said spacers are available in various sizes which sufficiently cover most of the spectrum of variability of the anatomical situations. However, it would be desirable if the medical user could individually adjust both the distance between the spacer head and the stem and the CCD angle (centrum-collum-diaphysis angle) during the revision surgery as a function of the anatomical situation encountered in each individual patient.

FR 2 948 012 A1 describes a hip implant, in which a head of the implant can be plugged onto a stem of the implant, whereby the head contains tanks that can be filled with antibiotic solutions prior to implantation. This is disadvantageous in that a lasting fixation of the head is not described in any detail and in that the angle of the head cannot be adjusted.

US 2013/072 896 A1 describes a generic modular hip spacer system, in which the distance between a spacer head and a spacer stem can be adjusted by screwing the spacer head, to different degrees, onto a thread on the spacer stem. The screw connection in this context is provided with an antibiotic coating. Permanent twist-proof fixation is afforded later by cementing with polymethylmethacrylate bone cement (PMMA bone cement).

This is disadvantageous in that the arrangement may change before the curing of the bone cement is completed. It is also disadvantageous that working with the bone cement during a surgery requires much effort, that bone cement residues becoming detached may contaminate the operating theatre, and that some tools, such as, for example, a spatula, need to be provided for application of the bone cement. Moreover, said system also does not allow the angle of the spacer head with respect to the spacer stem to be adjusted.

Accordingly, it is the object of the invention to overcome the disadvantages of the prior art. Specifically, an articular spacer system is to be provided that is easy to use, requires little effort in the often hectic workflow of a surgical theatre, and is not prone to handling errors. Moreover, an articular spacer system having a modular structure is to be provided, in which the distance between the spacer stem and the spacer head can be adjusted variably and in which, in addition, the CCD angle between spacer stem and spacer head can be varied. The articular spacer system is to be well-suited, in particular, for hip spacer systems. Another essential object of the invention is that the modules of the modular articular spacer system can be affixed very easily in irreversible and twist-proof manner after the medical user adjusts the distance between spacer stem and spacer head and of the CCD angle in a patient-specific manner. This means that the medical user is to be provided with a modular articulated spacer system that can be affixed according to the anatomical situation of the patient without changing its shape, in irreversible manner, and without requiring the use of special tools with the least possible expenditure of time and work resources. At the same time, the articulated spacer system is to be inexpensive.

The objects of the invention are solved by a modular articulated spacer system for screw-based assembly of an articular spacer intended to replace an artificial joint temporarily, whereby the articulated spacer system comprises at least two modules that can be connected by means of a screw connection, whereby a first module of the articular spacer system comprises a surface for formation of a sliding surface of the joint of the articular spacer and a second module of the articular spacer system comprises a stem for connection to a bone, in which the modules that can be connected by means of the screw connection comprise at least one screw-locking device for each screw connection, whereby the at least one screw-locking device is connected to one of the modules or is provided in the form of the same part as one of the modules.

The screw-locking devices can, for example, be implemented as wedge lock washers, which preferably are provided in the form of the same part as the modules. Alternatively, tooth locks, lock washers with ribs, spring washers or SCHNORR safety washers can be provided on the elements as screw-locking device. However, it is preferred according to the invention to use tooth lock washers as screw-locking device.

Preferably, the invention can provide the at least one screw-locking device to be firmly connected to one of the modules or to be provided in the form of the same part as a module. Theoretically, it might be sufficient to glue or weld the screw-locking device to the module in order to implement a connection to the module.

The articular spacers built-up using the articulated spacer system can, in particular, be hip spacers, knee spacers or elbow spacers. Accordingly, according to the invention, the articulated spacer system can be a hip spacer system, knee spacer system or elbow spacer system, whereby hip spacer systems are particularly preferred in the scope of the present invention since the variability of the articulated spacer system according to the invention has particularly beneficial effects in this case. Even minor mal-positions or deviations from optimal shape in an artificial hip joint, and thus in a hip spacer, can quickly lead to back pain and other ailments such that precise treatment of the patient, as afforded through the articulated spacer system according to the invention, is particularly important.

According to the invention, the elements of the screw connection are preferably a threaded rod having an external thread and a union nut having an internal thread.

The invention also proposes an articulated spacer system that comprises at least three modules that can be connected by means of screw connections, and two modules to comprise at least one screw-locking device.

As a result, the articular head, the stem, and the angle between the two can be adjusted independent of each other by means of separate modules, namely an articular head module, a stem module, and an adapter module. Due to this measure, articulated spacer systems are obtained that are particularly variable in use.

Moreover, the invention can just as well provide two screw-locking device parts for each screw connection, whereby these parts are firmly connected to the two modules to be connected by means of the screw connection or are provided in the form of the same part as the two modules to be connected by means of the screw connection, and whereby these engage each other appropriately when the modules are screwed together such that they resist any detachment of the screw connection, preferably prevent any detachment of the screw connection.

Providing two screw-locking device parts that engage each other, allows a particularly stable connection to be established, in particular from material of the same hardness.

Solutions involving different materials are less preferred, since metallic abrasion products from mechanical deformation of one component upon the screw-locking device parts being hooked into each other are to be prevented. Adhesive connections should also be avoided, since these are usually not sufficiently bio-compatible and might interfere with the healing process.

An embodiment of the invention proposes each screw connection to comprise an internal thread and an external thread that matches the internal thread. On the ends facing each other in the connected condition two modules can be connected to each other by means of a screw connection, whereby the internal thread and the external thread of said screw connection are designed appropriately such that the screw connection is a part of the two modules.

This is the simplest version of a screw connection.

In this context, the invention can provide the screw-locking device at the end of the external thread or at the start of the internal thread on one each of the modules that can be connected to each other, or the invention can provide a screw-locking device part at the end of the external thread or at the start of the internal thread on both modules that can be connected to each other.

As a result, it can be ensured that the screw-locking devices engage only when the modules are screwed together fully and that the modules become connected to each other in non-detachable manner.

Moreover, the invention can provide the modules to each comprise a metal core, whereby the metal core projects from one of the ends, which face each other, of the modules that can be connected to each other, and there forms the external thread, and can provide a hole with the internal thread in the metal core of the other module of the modules that can be connected to each other such that the external thread and the internal thread form a screw connection. It can be preferred in this context to provide the screw-locking device also to be formed by at least one of the metal cores, particularly preferably the screw-locking device to be formed by both metal cores.

The metal cores possess a stability that is very well-suited for medical purposes and allow a stable articular spacer to be built-up from the articulated spacer system. Moreover, the metals of the metal cores are very well-suited for providing the threads of the screw-locking device in the form of a single part and for providing suitable screw-locking devices.

It can be preferred according to the invention in this context that the metal cores consist of a chromium-cobalt steel or a V4A steel.

The one-part design ensures that the connection of a module to its screw-locking device part is particularly stable. Moreover, it allows the number of parts needed to be reduced which results in the articulated spacer system being particularly easy to use.

A refinement of the invention proposes the at least one screw-locking device to be two tooth lock washers or a two-part wedge lock.

Said screw-locking devices are particularly advantageous since they afford a stable reverse motion lock device and/or screw-locking device even without any plastic deformation and with no adhesives.

In this context, the invention can provide the flanks of the teeth of the tooth lock washers or the wedges of the wedge locks to be inclined against the direction of rotation of the elements of the at least one screw connection and the height of the teeth of the tooth lock washers or of the wedges of the wedge locks to be larger than the pitch of the threads of the elements of the at least one screw connection.

This allows for easy screw-based attachment and also for reliable locking against any attempt to detach the screw connection.

The invention can just as well provide the wedge locks to comprise radial ribs on the outside and wedge surfaces on the inside whose slope is larger than the pitch of the thread. Due to the radial ribs, tightening leads to a form-fit. The pair of wedge locks is then situated firmly in its place and only motions between the wedge surfaces can take place. Even slight rotation in detaching direction increases the clamping force due to the wedge effect and the screw connection secures thus itself by means of the screw-locking device.

The invention can just as well provide each screw connection and each screw-locking device to consist of a bio-compatible material.

Bio-compatible materials are well-suited for use in the human body.

According to an advantageous refinement, the invention can provide spacers between the modules in the form of tooth lock washers with teeth on both sides or wedge locks with wedges on both sides, whereby the spacers preferably consist of a metal having a lower Vickers hardness than the screw connection.

By this means, interlocking through deformation of the spacers can proceed and variable distancing of the modules can be attained by providing a multitude of spacers of different height. Interlocking associated with deformation is advantageous in that it is particularly stable, but it is disadvantageous in that plastic deformation is always associated with the risk of parts detaching.

According to a preferred embodiment, the invention can provide the articulated spacer system to be a hip spacer system and to comprise three modules, whereby the third module is an adapter module, which, in assembled condition, connects the first module and the second module at a distance from each other and in non-detachable manner.

In this context, the adapter module can be provided to be angled and the angle to be between 110° and 145°.

Moreover, all articulated spacer systems according to the invention can preferably be provided such that the outer surfaces of the modules, in assembled condition, are formed by a plastic material, in particular by a polymethylmethacrylate bone cement, whereby at least one anti-infective agent and/or antiseptic agent is or are suspended and/or dissolved in the plastic material and whereby the threads of the screw connections and screw-locking devices are not formed by the plastic material, but preferably consist of metal.

This enables the articular spacers built-up as described to have a medical effect without reducing their stability. Antibiotics are particularly preferred as anti-infective agents.

According to a preferred embodiment, the invention can provide the articular spacer system to consist of a bio-compatible material, which preferably comprises an envelope consisting of cured polymethylmethacrylate bone cement that contains at least one antibiotic and/or one antiseptic.

Said materials are particularly well-suited for use in the human body.

A refinement of the invention also proposes that the articulated spacer system comprises a multitude of different modules of the same function, but different external shape such that a multitude of different articular spacers can be assembled from said articulated spacer system.

In this context, the different shape is just a difference in the outward dimensions. The screw connections and the screw-locking devices of modules of the same type are identical such that the various modules still match the various other modules.

The objects of the invention are also solved by a method for building-up an articular spacer using said articulated spacer system, in which the articular spacer is screwed together using at least two modules, which are selected from a multitude of different modules to suit the anatomy and/or treatment situation, whereby the modules are screwed together appropriately such that the screw-locking devices prevent the modules from detaching or being unscrewed.

And lastly, the objects of the invention are also solved through the use of an articular spacer made from an articulated spacer system of this type as a temporary place-holder for an artificial joint.

The invention is based on the surprising finding that having the screw-locking devices enables the modules of a modular articulated spacer system to be firmly and definitively connected to each other for the purpose on hand by means of screw connections without any effort and without any need for fixation by means of bone cement. In this context, it is particularly preferable to use, as screw-locking devices, tooth lock washers or wedge locks, which preferably are provided in the form of the same part as the modules of the articulated spacer system. The invention also renders gluing of the modules unnecessary. Adhesives often have a disadvantageous effect on the healing process and are therefore disadvantageous.

The invention can be implemented, for example, through an articulated spacer system made of modules, whereby each module preferably possesses at least one metal core and said metal cores are provided on the end as elements of screw connections, at the ends of which the metal cores are provided in the shape of tooth lock washers or wedge lock parts. This means that the modules can be screwed to each other by means of the elements of the screw connections until the adjacent tooth washers or wedges rotate into each other. Due to over-rotating the flanks, which are arranged against the direction of rotation of the screw connection, the modules cannot be rotate in reverse. As a result, the modules are connected to each other in irreversible and twist-proof manner.

An articulating spacer system according to the invention consists, for example of at least two modules, whereby
a) each module contains at least one element of the screw connections;
b) each module is provided on the end of the at least one element of a screw connection as a tooth lock washer or wedge lock part, whereby the flanks of the teeth of the tooth lock washers or the wedges of the wedge lock parts are arranged against the direction of rotation of the at least one element of the screw connection;
c) the height of the teeth of the tooth lock washers or of the wedges of the wedge lock parts is larger than the pitch of the thread of the screw connections; and
d) the at least one element of the screw connections and the tooth lock washers or wedge lock parts consist of a bio-compatible material.

The invention can provide the screw connections and the tooth lock washers or wedge lock parts of each module to be connected to each other in a substance-to-substance bond, whereby the screw connections and the tooth lock washers or wedge lock parts are preferably provided in the form of the same part, i.e. in a one-part design.

Preferably, the modules each contain at least one metal core, whereby at least one end of the metal core is provided as external thread or internal thread, whereby the metal core is provided on one end of the at least one external thread or internal thread as a tooth lock washer or wedge lock part.

According to the invention, a hip spacer system according to the invention can be made up of a) a head module having a sliding surface;
b) a stem module; and
c) at least one adapter module, whereby said adapter module keeps the head module at a distance from the stem module.

In a further embodiment according to the invention, the hip spacer system is made up of a) a head module having a sliding surface;
b) a stem module; and
c) a curved adapter module that has a CCD angle of 110°-145°.

Using adapter modules having different CCD angles allows patients to be managed whose CCD angle deviates clearly from the very common CCD angle in Europe of 135°.

Moreover, the invention can provide tooth lock washers or wedge lock washers to be arranged between the modules as spacers and these to possess a serration on both sides, whereby said spacers preferably consist of a metal that has a lower Vickers hardness than the metal core of the modules. Said additional spacers are not part of the modules. Theoretically, simple washers made of a softer material can be used as spacer.

The invention can just as well provide the metal core to be fully or partly covered by a plastic material, in which one or more anti-infective agents and/or antiseptic agents are suspended and/or dissolved, whereby the external threads and/or the internal threads are not covered by a plastic material. Conceivable anti-infective agents include all common antibiotics with gentamicin, tobramycin, clindamycin, vancomycin, daptomycin, and fosfomycin being particularly preferred according to the invention. Polyhexanide, octenidine, chlorhexidine, and hydrogen peroxide-releasing salts or adducts are particularly preferred as antiseptics.

Exemplary embodiments of the invention shall be illustrated in the following on the basis of six schematic figures, though without limiting the scope of the invention. In the figures.

To some extent, identical or similar components are identified in the figures through the same reference numbers.

Figure 1:
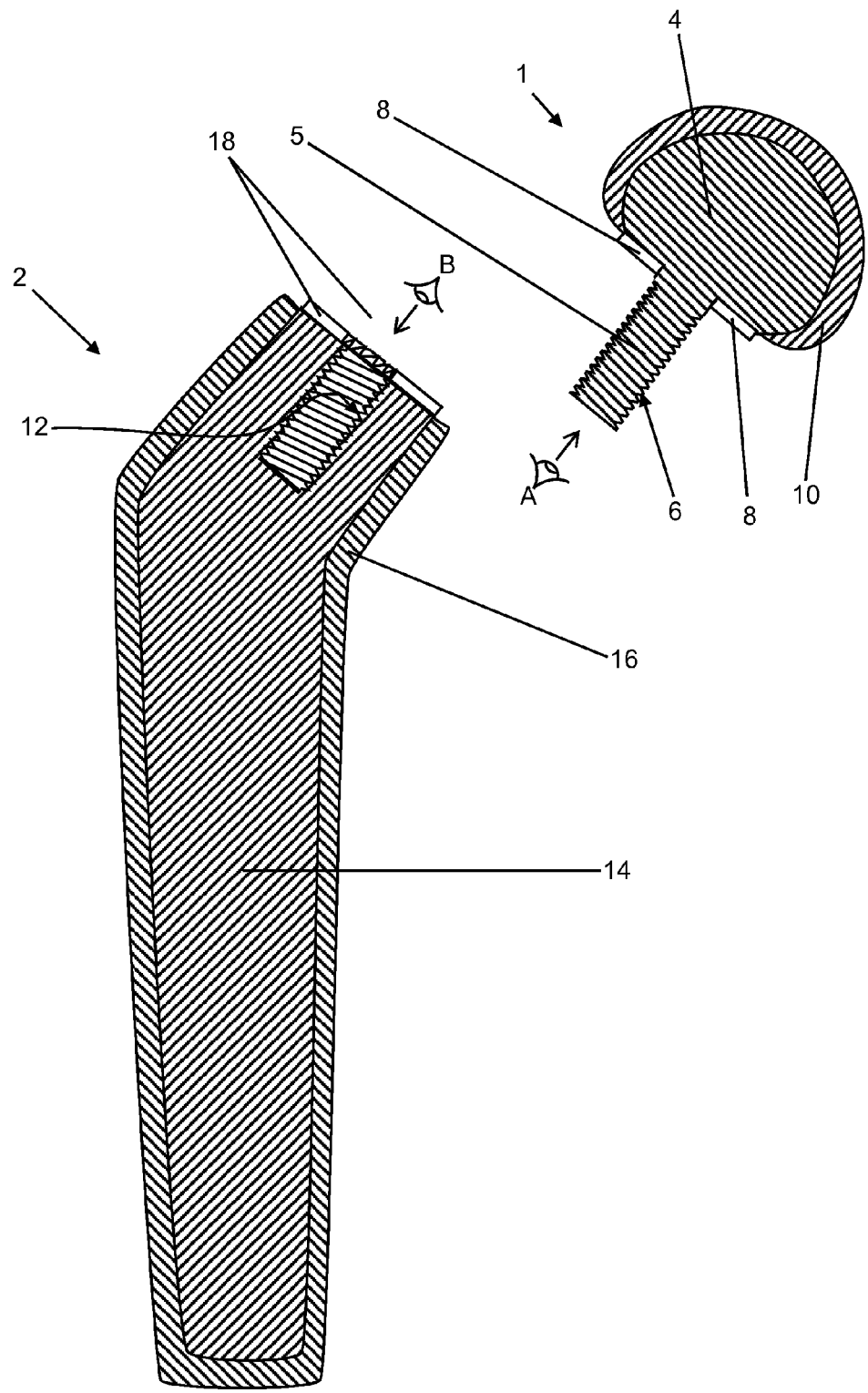
FIG. 1 shows a schematic cross-sectional view of the modules of a two-part hip spacer system according to the invention.

FIG. 1 shows a schematic cross-sectional view of the modules of a two-part hip spacer system according to the invention. The hip spacer system consists of an articular head module 1 and a stem module 2 that can be connected to each other by screws. The articular head module 1 consists, on its inside, of a metal core 4 that extends further as threaded rod 5 on the underside (facing downwards and to the left in FIG. 1) that is to be connected to the stem module 2. The threaded rod 5 has an external thread 6. The metal core 4 consists of a medical steel such as, for example, a chromium-cobalt steel.

A part of a wedge lock device 8, in which multiple wedges 8 are arranged on the metal core 4 circumferentially about the connection of the threaded rod 5 to the metal core 4, is situated on the underside of the articular head module 1 and forms the end of the threaded rod 5. Preferably, the wedges 8 are provided as single-parts or in the form of the same part as the metal core 4. Alternatively, the wedge lock device 8 can also be attached by gluing or soldering in said place. The wedges 8 of the wedge lock device 8 comprise one flat side and one vertical wedge surface.

The outside of the articular head module 1, which is to serve as sliding surface of the hip spacer, is fully covered by a plastic layer 10 made of a polymethylmethacrylate bone cement (PMMA bone cement). The PMMA bone cement contains a mixture of two antibiotics as anti-infective agent that can be dissolved from the PMMA bone cement and serves for treatment of an infection. Moreover, using the plastic layer 10 prevents metal parts from abrading and causing problems during the treatment.

The sliding surface, in inserted condition, touches against an acetabulum, which might also be artificial, and assumes the function of the hip joint in this place.

The stem module 2 is intended to be connected to a thigh bone of the patient. The stem module 2 comprises a bore hole matching the threaded rod 5 of the articular had module 1 or a matching cylindrical hole, in which an internal thread 12 matching the external thread 6 is provided. The hole provided with the internal thread 12 is contained in a metal core 14 of the stem module 2. The internal thread 12 and the external thread 6 as well as the hole and the threaded rod 5 form a screw connection by means of which the articular head module 1 can be connected to the stem module 2. In connected condition, the two modules 1, 2 of the hip spacer system form a hip spacer for temporary replacement of an artificial hip.

With the exception of the connecting surface of the stem module 2 to the articular had module 1 (pointing upwards to the right in FIG. 1), the surface of the stem module 2 is fully covered by a plastic layer 16 made of PMMA bone cement. The metal core 14 is exposed at the connecting surface of the stem module 2, from which the hole extends into the metal core 14 as well. The wedges 18 of the second part of the wedge lock device 18 are provided on the surface of the metal core 14 of the connecting surface and form a joint wedge lock device 18 together with the wedges 8 of the articular head module 1. For this purpose, the wedges 18 are arranged about the opening to the hole. The two parts of the wedge lock device 8, 18 engage each other when the articular head module 1 is screwed fully into the stem module 2 and prevent the connection from detaching by means of the vertical wedge surfaces of the wedges 8, 18.

Preferably, the wedges 18 are provided as single-parts or in the form of the same part as the metal core 14. Alternatively, the wedge lock device 18 can also be attached in said location by gluing or soldering. The wedges 18 of the wedge lock device 18 comprise one flat side and one vertical wedge surface, whereby the slopes and the heights of the flat wedge surfaces and vertical wedge surfaces are the same as those of the wedges 8 of the articular head module 1.

As a matter of principle, the wedges 8, 18 form a matching pair of wedge lock washers, whereby the wedge lock washers are firmly connected to the metal cores 4, 14 of the two modules 1, 2 at the base of their threads 6, 12 of the screw connection or preferably are even provided in the form of the same part as the metal cores 4, 14 of the two modules 1, 2 on the basis of their threads 6, 12 of the screw connection.

The stem module 2 is angled at a CCD angle of 142° and thus replicates the shape of a specific thigh bone that is not typical in Europe. Alternatively, a different stem module (not shown) having a different CCD angle can be selected just as well, for example one having the standard angle in Europe of 135°. Just as well, instead of the articular head module 1, a different articular head module (not shown) having a different shape and/or size can be selected. For treatment, a multitude of different stem modules and articular head modules are available as sets, but always have the same thread bore holes and threaded rods 5 and thus are always compatible with each other, i.e. can be screwed together. By means of this measure, different shapes of hip spacers can be generated using the hip spacer system. In this context, the screw-locking device 8, 18 formed by the wedge lock device 8, 18 ensures that the two modules 1, 2 can no longer be detached from each other without any need to cement the two parts.

Figure 2:
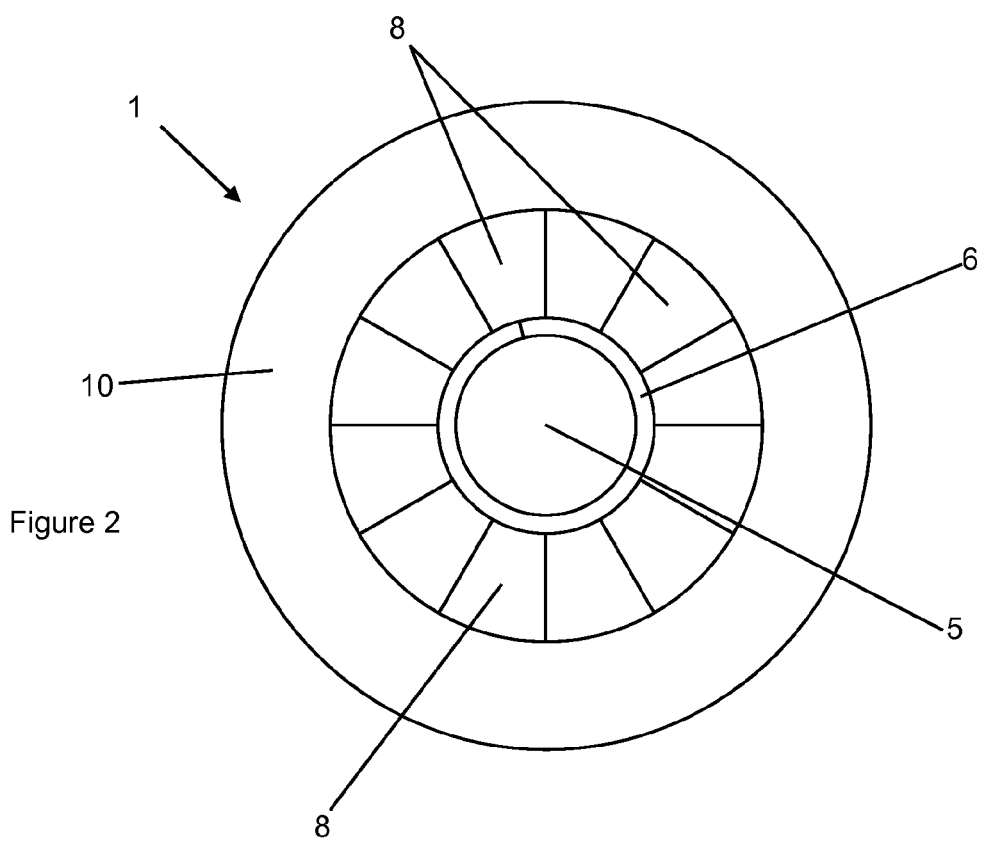
FIG. 2 shows a schematic top view in viewing direction A onto the connection side of the articular head module according to FIG. 1.
Figure 3:
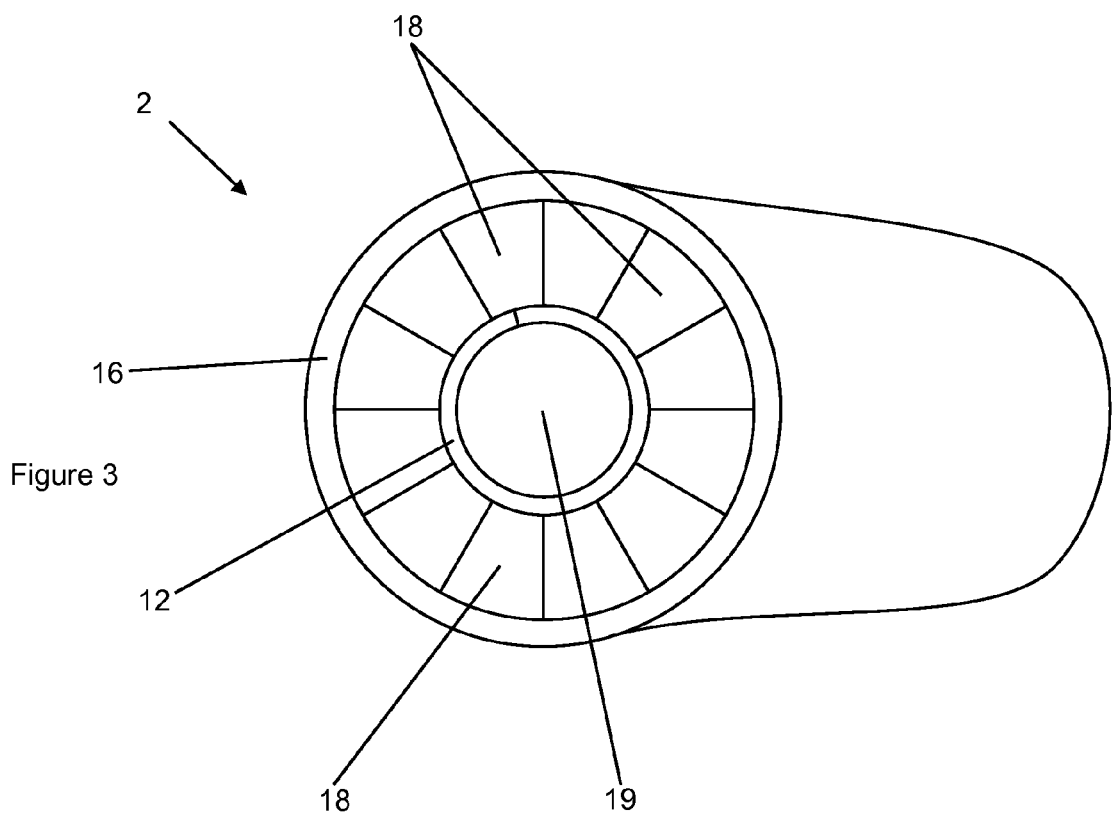
FIG. 3 shows a schematic top view in viewing direction B onto the corresponding connection side of the stem module according to FIG. 1.

FIG. 2 shows a schematic top view in viewing direction A onto the connection side of the articular head module 1 according to FIG. 1 and FIG. 3 shows a schematic top view in viewing direction B onto the corresponding connection side of the stem module 2 according to FIG. 1. Viewing directions A and B are indicated in FIG. 1 by a schematically depicted eye in order to illustrate the viewing direction.

In FIG. 2, the threaded rod 5 points towards the observer (out of the image plane). The external thread 6 can be seen to be situated on the outside around the threaded rod 5. Analogously, the hole 19 and/or the tapped hole 19 extends vertically from the image plane into the image plane, i.e. away from the observer. The internal thread 12 can be seen on the edge of the hole 19.

The wedges 8, 18 are concentric and are arranged about the threaded rod 5 and/or the tapped hole 19 with a twelve-fold rotational symmetry axis with respect to the symmetry axis of the threaded rod 5 and tapped hole 19. The vertical lines between the wedges 8, 18 of the wedge lock parts 8, 18 correspond to the vertical wedge surfaces of the wedges 8, 18. The surfaces correspond to a view onto the flat wedge surfaces.

The extension on the stem module 2 that extends towards the right in FIG. 3 is the angled stem of the stem module 2. By means of a set of modules 1, 2 that includes stem module 2 and articular head module 1 of different external shapes and dimensions, hip spacers that are adapted to the needs of the treatment situation on hand can be produced easily. Using screw-locking devices 8, 18 according to the invention allows hip spacers screwed together as described to be inserted directly into the patient without any need for additional fixation of the two modules 1, 2.

Figure 4:
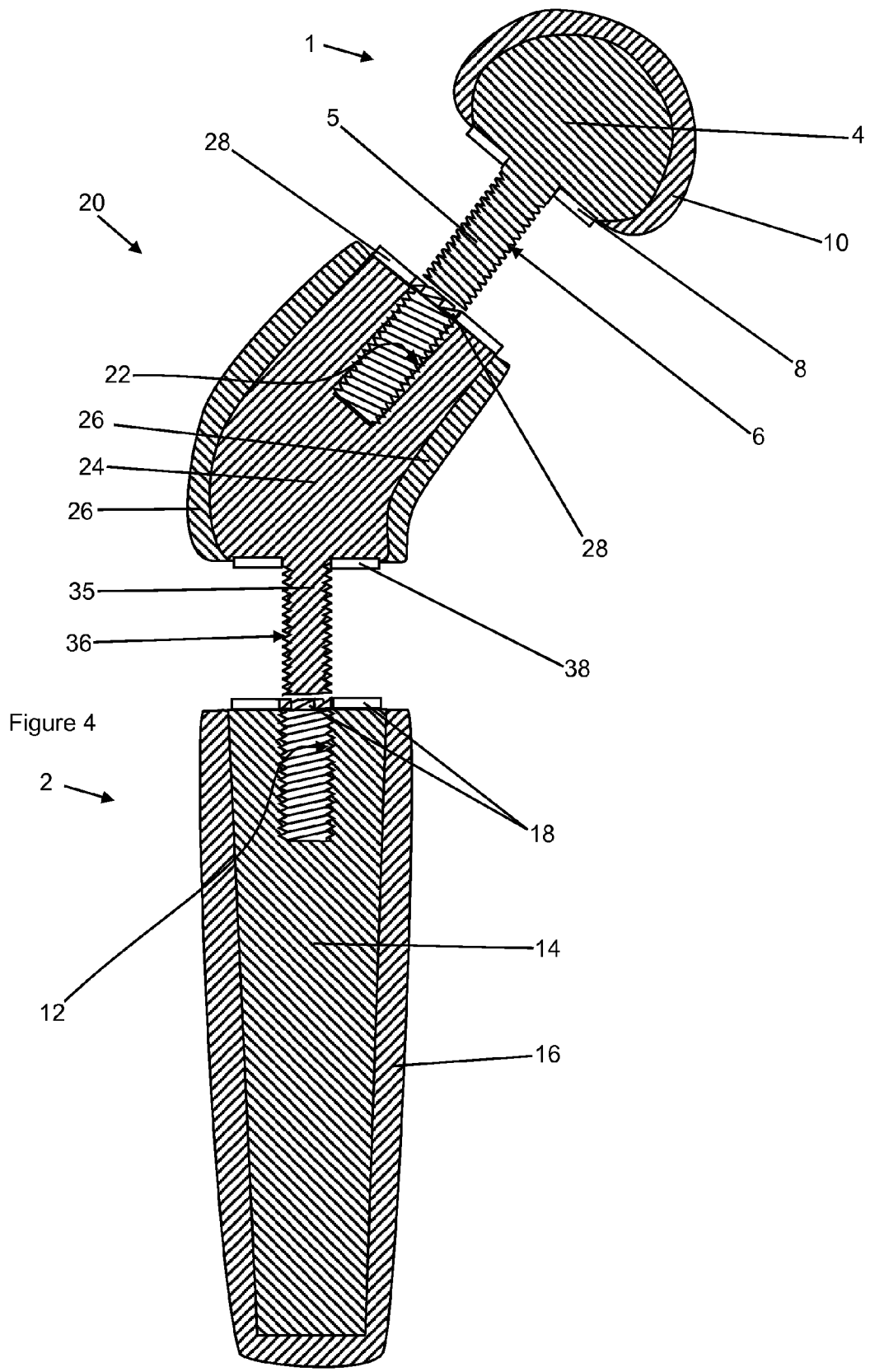
FIG. 4 shows a schematic cross-sectional view of the modules of a three-part hip spacer system according to the invention.

FIG. 4 shows a schematic cross-sectional view of the modules of a three-part hip spacer system according to the invention. The hip spacer system according to FIG. 4 differs from the one according to FIGS. 1 to 3 in that a third module 20, namely an adapter module 20, is provided in addition to an articular head module 1 and a stem module 2.

The articular head module 1 is designed analogous to the articular head module according to FIGS. 1 and 2. A V4A steel is used presently as the steel for the metal core 4, threaded rod 5, and wedges 8. The sliding surface and the outside, except for the connecting surface to the adapter module 20, are covered by PMMA bone cement containing at least one pharmaceutically active substance.

Unlike the stem module according to FIGS. 1 and 3, the stem module 2 has no CCD angle, since same is defined presently by means of the adapter module 20. The stem module 2 according to FIG. 4 comprises a metal core 14 and wedges 18 of a wedge lock device made of a V4A steel that is covered by a PMMA bone cement on its outside, except for the connecting surface to the adapter module (on the top in FIG. 4). A tapped hole having an internal thread 12 is provided in the metal core 14.

The adapter module 20 has a tapped hole having an internal thread 22 for connection to the articular head module 1. The tapped hole is provided in a metal core 24 made of a V4A steel (for example 1.4401, 1.4404 or 1.4571). The metal cores 4, 14, 24 consist of the same V4A steel.

Except for the connecting surface to the articular head module 1 (towards the top right in FIG. 4) and the connecting surface to the stem module 2 (downwards in FIG. 4), the outside of the adapter module 20 is enveloped by a PMMA bone cement 26. The PMMA bone cement envelopes 10, 16, 26 contain at least one antibiotic and/or at least one antiseptic agent that can be dissolved from the PMMA bone cement envelopes 10, 16, 26 to treat the surrounding human tissue, in patient-inserted condition, for a period of several days or weeks.

Wedges 28 are arranged on the connecting surface to the articular head module 1 in concentric and rotationally symmetrical manner about the tapped hole and match the wedges 8 of the articular head module 1 and form a wedge lock device together with the wedges 8. A threaded rod 15 having an external thread 36 matching the internal thread 12 of the stem module 2 is provided on the connecting surface to the stem module 2. Likewise, wedges 38 matching the wedges 18 of the stem module 2 and forming a second wedge lock device together with these are provided on the connecting surface to the stem module 2.

When the modules 1, 2, 20 are screwed into each other, the wedges 8, 28 and the wedges 18, 38 engage each other and become connected to each other. Due to the form-fit of the wedges 8, 28 and wedges 18, 38, the modules 1, 2, 20 can no longer be unscrewed. The vertical sides (flanks) of the wedges 8, 28 and wedges 18, 38 resist the rotary motion upon detachment of the screw connection, whereas the flat sides of the wedges 8, 28 and wedges 18, 38 can still slide one over the other when the screw connections 8, 18, 28, 38 are being screwed together such that the interlocking is established only upon detachment of the screws.

The side views of the internal threads 12, 22 are shown on the inside of the tapped holes according to FIGS. 1 and 4, i.e. the structures on the inside of the tapped holes are not cross-hatching to depict a sectioned material, but are actually the grooves of the internal threads 12, 22. In the cross-sectional views, the sectioned surfaces of the articulated spacer systems and/or of the modules 1, 2, 20 are always shown by cross-hatching.

Figure 5:
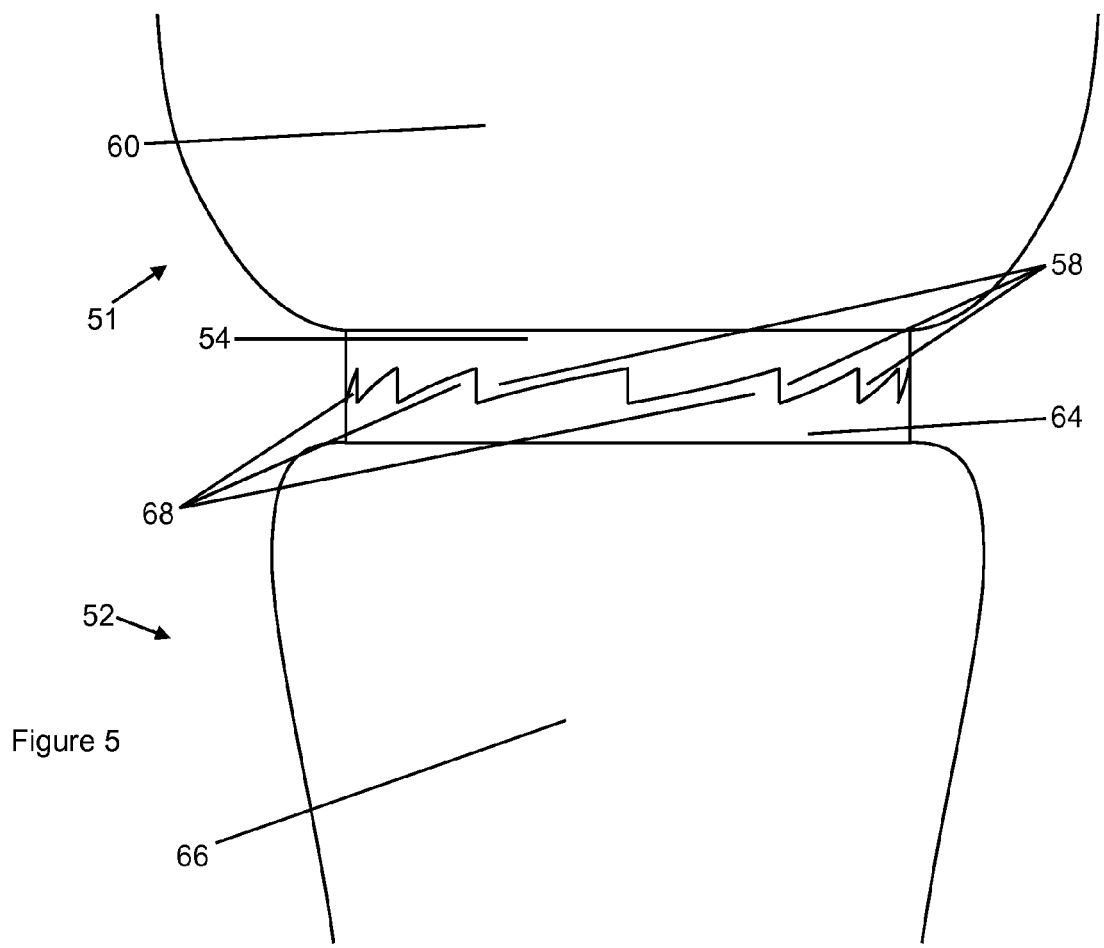
FIG. 5 shows a schematic side view of a detail of the connection site of two connected modules of an articulated spacer system according to the invention.

FIG. 5 shows a schematic side view of a detail of the connection site of two connected modules 51, 52 of an articulated spacer system according to the invention. The modules 51, 52 each comprise, on the surfaces facing each other, one part of a pair of wedge lock washers 54, 64 that are attached to the modules 51, 52. Each wedge lock washer 54, 64 comprises, on the surfaces facing each other, wedges 58, 68 that engage each other in assembled condition.

One of the wedge lock washers 54, 64 can be supported as in a bearing on one of the modules 51, 52 such that it can rotate, whereby the wedge lock washer 54, 64 either locks when exposed to sufficient pressure due to the screw-based assembly or it is pressed against the module 51, 52 due to the contact pressure after screw-based assembly. As a result, it can be ensured that the wedge lock washers 54, 64 engage each other easily. Rotatability of the one of the wedge lock washers 54, 64 is not necessary, since the elastic deformation of the wedges 58, 68 is sufficient for the wedges 58, 68 to engage each other appropriately such that they can no longer be detached in the opposite direction of rotation.

The steep (perpendicular) flanks of the wedges 58, 68 are oriented against the direction of rotation of the screw connection of the two modules 51, 52 and the pitch of the thread of the screw connection is smaller than the height of the wedges 58, 68 of the wedge lock washers 54, 64. The modules are covered on the outside by a PMMA bone cement 60, 66 containing soluble antibiotics.

As an alternative to the wedge lock devices shown in the embodiments according to FIGS. 1 to 5, other screw-locking devices can be used just as well to prevent modules that have been screwed into each other from detaching. For example, serrated ratchets made of a hard metal can be provided that embed themselves in a softer region at the base of the tapped hole or of the threaded rod and prevent a reverse rotation. A spring-actuated Schnorr safety washer can be connected to one side to the metal core at the base of the threaded rod (for example can be attached by welding). The teeth (and/or wedges) of the spring-actuated Schnorr safety washer can either engage a spring-actuated Schnorr safety washer on the other module to be connected and connect to it or the teeth can be sunk into a softer material of the opposite metal core. Due to the spring properties, the modules can be connected to each other more easily and with less force.

Figure 6:
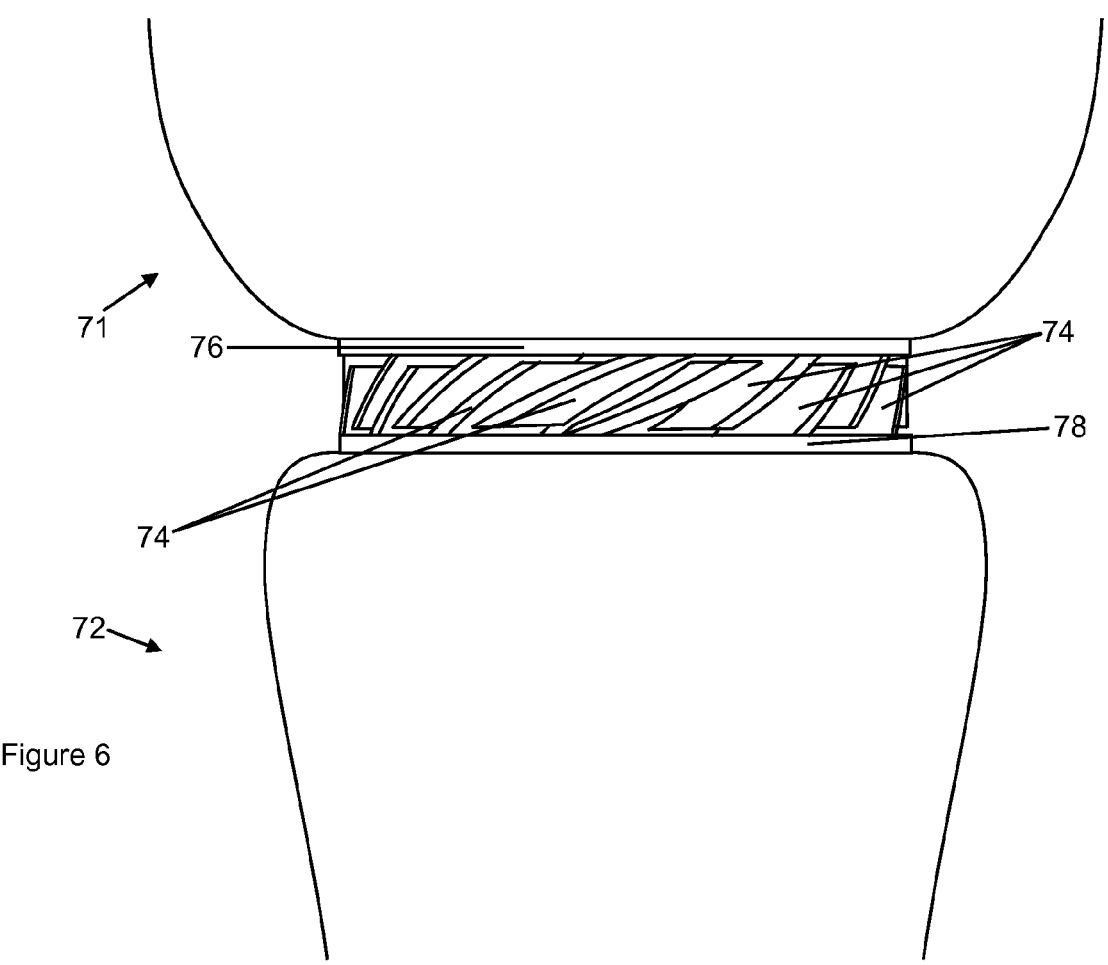
FIG. 6 shows a schematic side view of a detail of the connection site of two connected modules of another articulated spacer system according to the invention.

FIG. 6 shows a schematic side view of a detail of the connection site of two connected modules 71, 72 of an articulated spacer system according to the invention, in which oblique elastic metal washers 74 of the type of tooth lock washers are connected to the modules 71, 72 as screw-locking devices. The metal washers 74 are equivalent to the wedges 8, 18, 28, 38, 58, 68 according to FIGS. 1 to 5 and assume the same function, whereby the vertical surfaces are missing in the present case and the oblique flanks are formed by one side of the metal washers 74.

The metal washers 74 are the teeth 74 of the tooth lock washers. As a result, the metal washers 74 can undergo an elastic deformation when they are screwed together (upper module 71 is rotated towards the right, i.e. counter-clockwise, against the lower module 72), whereas the metal washers 74 of the modules 71, 72 engage each other and prevent the modules 71, 72 from detaching when they are unscrewed (upper module 71 rotates towards the left, i.e. clockwise against the lower module 72)).

The metal washers 74 are arranged rotationally symmetrical with respect to a central screw connection (threaded rod and tapped hole, not shown in FIG. 6). The metal washers 74 are welded along their upper edges, at the inclination angles shown, to a metal core 76 of the lower module 71 and are welded at their lower edges to a metal core 78 of the lower module 72 or, preferably, are structured to be the same part as the respective metal cores 76, 78.

Due to their elasticity, the metal washers 74 can be screwed into each other. Upon any attempt to detach the modules 71, 72 through a rotation in the opposite direction, the metal discs 74 engage each other and block the rotation. The modules 71, 72 are then connected to each other in non-detachable manner.

The features of the invention disclosed in the preceding description and in the claims, figures, and exemplary embodiments, can be essential for the implementation of the various embodiments of the invention both alone and in any combination.

LIST OF REFERENCE NUMBERS

1, 51, 71 Articular head module/first module
2, 52, 72 Stem module/second module
4, 14, 24 Metal core
5, 35 Threaded rod
6, 36 External thread
8, 18, 28, 38 Wedge/wedge lock device
10, 16, 26 Plastic layer
12, 22 Internal thread
19 Hole/tapped hole
20 Adapter module/third module
54, 64 Metal core
58, 68 Interlocking
60, 66 PMMA envelope
74 Metal washer
76, 78 Metal core
A Viewing direction of the top view according to FIG. 2
B Viewing direction of the top view according to FIG. 3

The invention claimed is:
1. A modular articular spacer system for screw-based assembly of an articular spacer for replacing an artificial joint temporarily, wherein the articular spacer system comprises at least two modules that are connectable by means of at least one screw connection, whereby a first module of the articular spacer system comprises a first core fully covered by an outer layer of the first module except at a first connecting surface of the first module, wherein the first core is exposed at the first connecting surface of the first module, whereby the first module further comprises a curved sliding surface of the joint of the articular spacer, whereby a second module of the articular spacer system comprises a second core fully covered by an outer layer of the second module except at a second connecting surface of the second module, wherein the second core is exposed at the second connecting surface of the second module, whereby the second module further comprises a stem for connection to a bone, wherein the first and second modules are directly connectable by means of the at least one screw connection that comprises at least one screw-locking device for each screw connection, wherein the at least one screw-locking device comprises a first part provided at the first connecting surface of the first module and a second part provided at the second connecting surface of the second module, wherein, if the first and second modules are directly connected, the first connecting surface of the first module is facing towards the second connecting surface of the second module, wherein a majority of the outer layer of the first module consists of the curved sliding surface that terminates at the first part of the at least one screw-locking device, wherein the curved sliding surface has a bulbous shape that (i) is formed by continuous and uninterrupted curved surfaces that extend along the majority of the outer layer of the first module and (ii) terminates at the first connecting surface of the first module comprising the first part of the at least one screw-locking device, wherein the first and second parts of the at least one screw-locking device are provided for each screw connection, wherein the first part of the at least one screw-locking device is fixedly connected to the first core at the first connecting surface of the first module and the second part of the at least one screw-locking device is fixedly connected to the second core at the second connecting surface of the second module, wherein the first and second parts engage each other when the at least two modules are screwed together such that any detachment of the screw connection is resisted or prevented.

2. The articular spacer system according to claim 1, wherein the screw connection comprises an internal thread and an external thread that matches the internal thread, and, on ends facing each other in the connected condition, the first and second modules are connectable to each other by means of the screw connection, wherein the internal thread and the external thread of the screw connection are configured such that the screw connection is a part of the first and second modules.

3. The articular spacer system according to claim 2, wherein the at least one screw-locking device is provided at an end of the external thread or at a start of the internal thread on one of the first and second modules that are connectable to each other, or the at least one screw-locking device is provided at the end of the external thread or at the start of the internal thread on both of the first and second modules that are connectable to each other.

4. The articular spacer system according to claim 3, wherein each of the first core of the first module and the second core of the second module is a metal core, wherein each metal core projects from one end of the first and second modules, which face each other, wherein one metal core forms the external thread, wherein a hole with the internal thread is provided in the other metal core such that, when the first and second modules are connectable to each other, the external thread and the internal thread form the at least one screw connection.

5. The articular spacer system according to claim 1, wherein the at least one screw-locking device is two tooth lock washers or a multiplicity of lockable wedges.

6. The articular spacer system according to claim 5 wherein the lockable wedges are provided and are inclined against a direction of rotation of elements of the at least one screw connection and a height of the lockable wedges is larger than a pitch of threads of the elements of the at least one screw connection.

7. The articular spacer system according to claim 1, wherein the at least one screw connection consists of a bio-compatible material.

8. The articular spacer system according to claim 1, wherein spacers are provided between the first and second modules in the form of tooth lock washers with teeth on both sides or wedge locks with lockable wedges on both sides.

9. The articular spacer system according to claim 1, wherein outer layers of the first and second modules are formed by a plastic material, wherein at least one of an anti-infective agent and an antiseptic agent is or are at least one of suspended and dissolved in the plastic material, wherein threads of the at least one screw connection are not formed by the plastic material.

10. The articular spacer system according to claim 1, wherein the articulated spacer system comprises a multitude of different modules having a same function and different external shapes such that the articulated spacer system is adapted to assemble a multitude of different articular spacers.

11. The articulate spacer system according to claim 1, wherein the articular spacer system provides an articular spacer as a temporary place-holder for an artificial joint.

12. The articular spacer system according to claim 4, wherein the at least one screw-locking device is formed by both of the first and second cores of the first and second modules.

13. The articular spacer system according to claim 8, wherein the spacers consist of a metal having a lower Vickers hardness than the at least one screw connection.

14. The articular spacer system according to claim 9, wherein the plastic material is a polymethylmethacrylate bone cement.

15. The articulate spacer system according to claim 1, wherein the bulbous-shaped curved sliding surface has a total length defined between the first part of the at least one screw-locking device and a tip region located opposite with respect to the first part of the at least one screw-locking device, wherein the diameter of the bulbous-shaped curved sliding surface continuously changes along the total length of the bulbous-shaped curved sliding surface.

16. A modular articular spacer system for screw-based assembly of an articular spacer for replacing an artificial joint temporarily, whereby the articular spacer system comprises at least two modules that are directly connectable by means of a screw connection, whereby a first module of the articular spacer system comprises an outer layer fully covering the first module except at a first connecting surface of the first module, whereby the first module further comprises a curved sliding surface of the joint of the articular spacer, whereby a second module of the articular spacer system comprises an outer layer fully covering the second module except at a second connecting surface of the second module, whereby the second module further comprises a stem for connection to a bone, wherein the first and second modules are directly connectable by means of the screw connection comprising at least one screw-locking device for each screw connection, wherein the at least one screw-locking device comprises wedges that are concentric and arranged about at least one of a rod and a hole with a twelve-fold rotational symmetry axis with respect to the symmetry axis of the rod and hole, wherein a majority of the outer layer of the first module consists of the curved sliding surface that terminates at a first part of the at least one screw-locking device at the first connecting surface of the first module, wherein the curved sliding surface has a bulbous shape that (i) is formed by a continuous and uninterrupted curved surfaces that extend along the majority of the outer layer of the first module and (ii) terminates at the wedges of the at least one screw-locking device, wherein the first and second parts of the at least one screw-locking device are provided for each screw connection, whereby the first part of the at least one screw-locking device is fixedly connected to a first core exposed at the connecting surface of the first module and the second part of the at least one screw-locking device is fixedly connected to a second core exposed at the connecting surface of the second module, wherein the first and second parts engage each other when the at least two modules are screwed together such that any detachment of the screw connection is resisted or prevented.

17. A modular articular spacer system for screw-based assembly of an articular spacer for replacing an artificial joint temporarily, wherein the articular spacer system comprises a first module, a second module and at least one third module that are connectable together by means of more than one screw connection, whereby the first module comprises a first core fully covered by an outer layer of the first module except at a first connecting surface of the first module, whereby the first module further comprises a curved sliding surface of the joint of the articular spacer, whereby the second module comprises a second core fully covered by an outer layer except at a second connecting surface of the second module, whereby the second module further comprises a stem extending to a distal end of the second module, wherein the second core extends from a proximal end of the second module, located opposite the distal end of the second module, through the stem of the second module to the distal end of the second module, wherein the first, second and third modules are connectable by means of the more than one screw connection that comprises at least one screw-locking device for each screw connection, wherein the at least one screw-locking device comprises a first part provided at the first connecting surface of the first module and a second part provided at the second connecting surface of the second module or an exposed third connecting surface of the third module, wherein, if the first and second modules are connected or the first and third modules are connected, the first connecting surface of the first module is facing towards the second connecting surface of the second module or the exposed third connecting surface of the third module, wherein a majority of the outer layer of the first module consists of the curved sliding surface that terminates at the first part of the at least one screw-locking device at the first connecting surface of the first module, wherein the curved sliding surface has a bulbous shape that (i) is formed by continuous and uninterrupted curved surfaces that extend along the majority of the outer layer of the first module and (ii) terminates at the first connecting surface of the first module comprising the first part of the at least one screw-locking device, wherein the first part of the at least one screw-locking device is fixedly connected to the first core at the first connecting surface of the first module and the second part of the at least one screw-locking device is fixedly connected to the second core at the second connecting surface of the second module or a third core at the exposed third connecting surface of the third module.

18. A method for building-up an articular spacer using the articular spacer system according to claim 1, the method comprising:

screwing the articular spacer, according to claim 1, together using at least the first and second modules, which are selected from a multitude of different modules to suit at least one of an anatomy and a treatment situation, wherein the first and second modules are screwed together appropriately such that the at least one screw-locking device prevents the first and second modules from detaching or being unscrewed.

* * * * *